Figure 1:
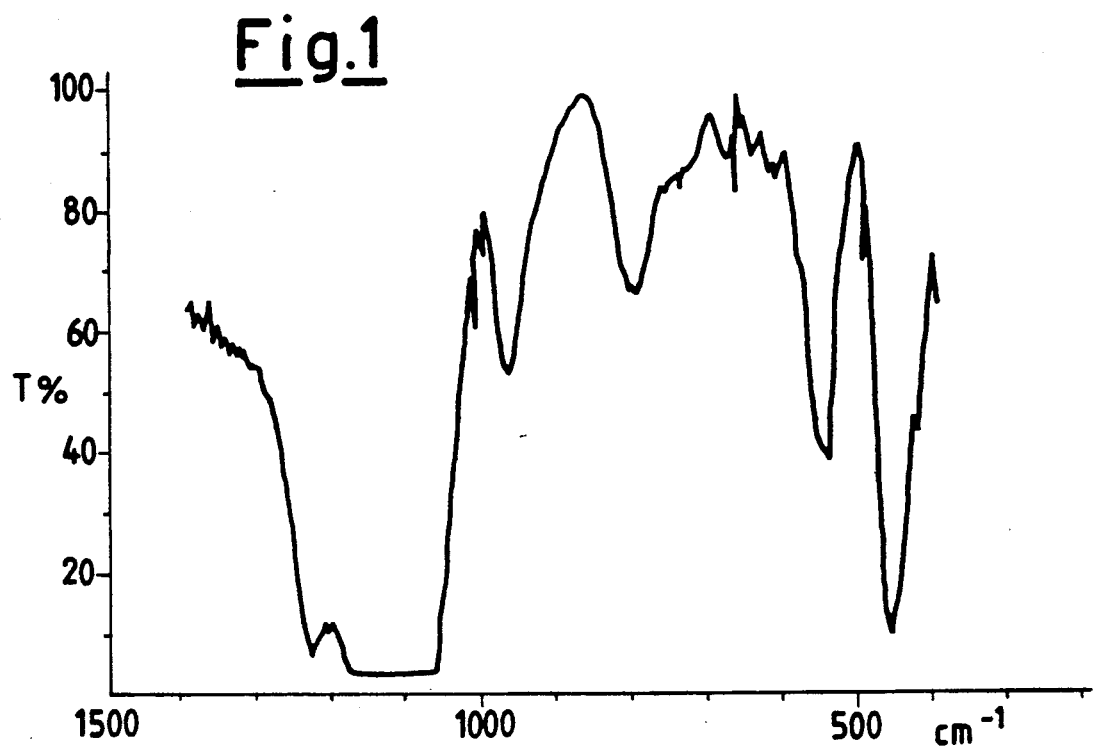

United States Patent
Bellussi et al.

[11] Patent Number: 5,290,533
[45] Date of Patent: *Mar. 1, 1994

[54] METHOD FOR PRODUCTION OF A COATED SUBSTRATE WITH CONTROLLED SURFACE CHARACTERISTICS

[75] Inventors: Giuseppe Bellussi, Piacenza; Mario G. Clerici, San Donato Milanese; Aldo Giusti, Lucca; Franco Buonomo, San Donato Milanese, all of Italy

[73] Assignees: Eniricerche S.p.A., Milan; Enichem Synthesis S.p.A., Palermo; Snamprogetti S.p.A., Milan, Italy

[*] Notice: The portion of the term of this patent subsequent to Sep. 21, 2010 has been disclaimed.

[21] Appl. No.: 750,240

[22] Filed: Aug. 16, 1991

Related U.S. Application Data

[63] Continuation of Ser. No. 548,196, Jul. 5, 1990, abandoned, which is a continuation of Ser. No. 434,558, Nov. 8, 1989, abandoned, which is a continuation of Ser. No. 943,544, Dec. 17, 1986, abandoned.

[30] Foreign Application Priority Data

Dec. 19, 1985 [IT] Italy ............................... 23292 A/85

[51] Int. Cl.$^5$ ............................................. C01B 33/34
[52] U.S. Cl. ................................. 423/704; 423/713; 423/DIG. 22; 502/77
[58] Field of Search ............... 423/326, 328, 329, 330, 423/332, 704, 713, DIG. 22, 700; 502/77

[56] References Cited

U.S. PATENT DOCUMENTS

| | | | |
|---|---|---|---|
| 4,410,501 | 10/1983 | Taramasso et al. | 423/326 |
| 4,452,909 | 6/1984 | Yang | 423/326 |
| 4,513,091 | 4/1985 | Chang et al. | 502/77 |
| 4,622,308 | 11/1986 | Koikeda et al. | 502/77 |
| 4,666,692 | 5/1987 | Taramasso et al. | 423/326 |
| 4,670,412 | 6/1987 | Chang et al. | 502/77 |

FOREIGN PATENT DOCUMENTS

| | | | |
|---|---|---|---|
| 1180312 | 1/1985 | Canada | 423/328 |
| 2403975 | 4/1979 | France | |
| 2471950 | 6/1981 | France | |

*Primary Examiner*—R. Bruce Breneman
*Attorney, Agent, or Firm*—Shea & Gould

[57] ABSTRACT

A crystalline, porous, synthetic material is disclosed, together with its related preparation process.

Such a material of zeolitic character, containing silicon, titanium and iron oxides, corresponds, in its calcined and anhydrous state, to the following empirical formula $$pHFeO_2 \cdot qTiO_2 \cdot SiO_2$$

wherein p has a value greater than zero and lower than or equal to 0.050, q has a value greater than zero and lower than or equal to 0.025, and the H$^+$ of HFeO$_2$ can be at least partly replaceable or replaced by cations.

17 Claims, 2 Drawing Sheets

METHOD FOR PRODUCTION OF A COATED SUBSTRATE WITH CONTROLLED SURFACE CHARACTERISTICS

This application is a continuation of U.S. patent application Ser. No. 07/548,196, filed Jul. 5, 1990, now abandoned, which is a continuation of U.S. patent application Ser. No. 07/434,558, filed Nov. 8, 1989, now abandoned, which is a continuation of U.S. patent application Ser. No. 06/943,544, filed Dec. 17, 1986, now abandoned.

The present invention relates to a synthetic material containing silicon oxide, titanium oxide and iron oxide, having a crystalline, porous, structure of zeolitic character and to the process for the preparation of such a material.

Such a material is structurally similar to ZSN-5 zeolite as disclosed in U.S. Pat. No. 3,702,886 patent, formally constituted, in its calcined and anhydrous form, by $M_{2/n}O, SiO_2, Al_2O_3$ (with M=cation with n valency).

Other synthetic materials, structurally correlated to ZSM-5 zeolite are known, such as the one as disclosed in U.S. Pat. No. 4,061,724 patent, formally constituted, in its calcined and anhydrous form, by $SiO_2$; the one as disclosed in BE-886,812, formally constituted, in its calcined and anhydrous form, by $SiO_2$ and $TiO_2$; and the one as disclosed in FR-2,403,975 patent application, formally constituted, in its calcined and anhydrous form, by $M_{2/n}O$, $SiO_2$, $Fe_2O_3$ (with M=cation of n valency).

A novel synthetic zeolite has been found now, which we'll denominate "titanium-iron-silicalite", structurally similar to silicalite, which can be used either as molecular sieve or as ion exchanger, or as catalyst in the following reactions: cracking, selectoforming, hydrogenations and dehydrogenations, oligomerizations, alkylations, isomerizations, dehydrations of oxygen-containing organic compounds—selective hydroxylations of organic substrates by $H_2O_2$ (oxidation of olefins, hydroxylations of aromatics).

The synthetic, crystalline, porous material of zeolitic character, containing silicon, titanium and iron oxides, which is the object of the present invention, corresponds, in its calcined and anhydrous state, to the following empirical formula:

$$pHFeO_2.qTiO_2.SiO_2$$

wherein p has a value higher than zero and lower than or equal to 0.050 and q has a value higher than zero and lower than or equal to 0.025, and the $H^+$ of $HFeO_2$ can be at least partly replaceable or replaced by cations.

The passage from a cationic form to another cationic form can be performed by any customary exchange processes of the known art.

The synthetic material in accordance with the present invention results crystalline on X-ray examination.

Such an examination has been carried out by means of a powder diffractometer, equipped with an electronic impulse counter system, by using CuK-α radiation. For the computation of the intensity values, the peak heights have been measured, and their percent heights relatively to the most intense peak have been computed.

The main reflections for the calcined and anhydrous product are characterized by the following d values (wherein d is the interplanar distance):

| d (Å) 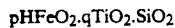 | Relative Intensity |
|---|---|
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw |

(wherein: vs=very strong; s=strong; m=medium, mw=medium-weak).

Such a diffraction spectrum is essentially similar to that of ZSM-5 and consequently of the other zeolites structurally correlated to ZSM-5, which have been mentioned in the introduction.

The material disclosed by ourselves shows an I.R. spectrum characterized by the following most representative values of wn (wherein "wn" is the wave number):

| wn cm$^{-1}$ | Relative Intensity |
|---|---|
| 1220-1230 | w |
| 1080-1110 | s |
| 965-975 | mw |
| 795-805 | mw |
| 550-560 | m |
| 450-470 | ms |

(wherein: s=strong; ms=medium-strong; m=medium, mw=medium-weak; w=weak).

In FIG. 1 the I.R. spectrum is shown of the calcined and anhydrous zeolitic material of the present invention, wherein on the abscissae the wave number in cm$^{-1}$ and on the ordinates the percent transmittance are expressed.

Figure 2:
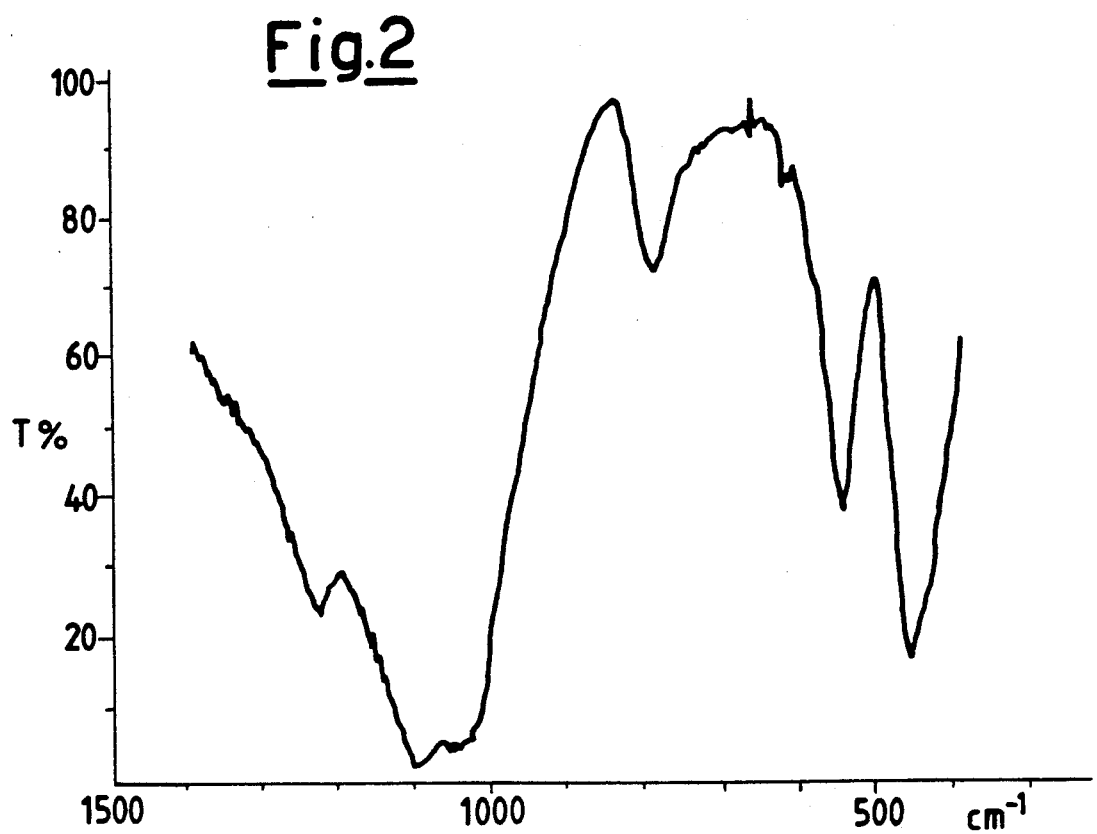

In FIG. 2, the I.R. spectrum of ZSM-5, or of similar structure, is shown.

Figure 3:
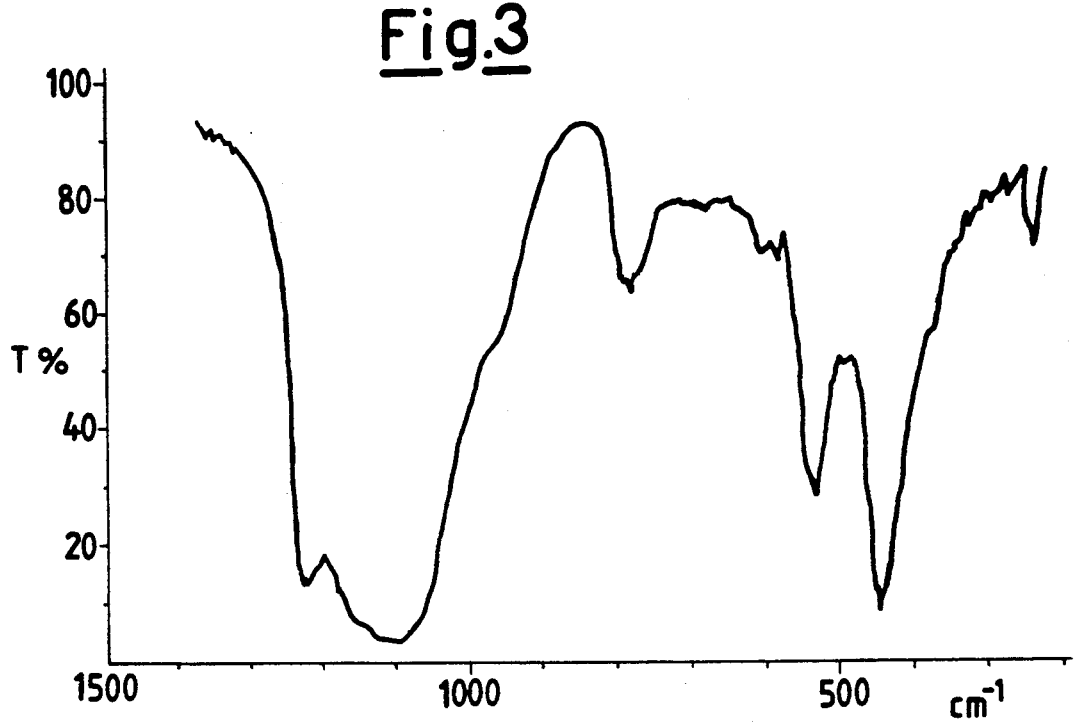

In FIG. 3, the I.R. spectrum of a product of comparison Example 8 is shown wherein the $M^+/SiO_2$ molar ratio is 0.08 and the crystallization time is 15 hours.

Figure 4:
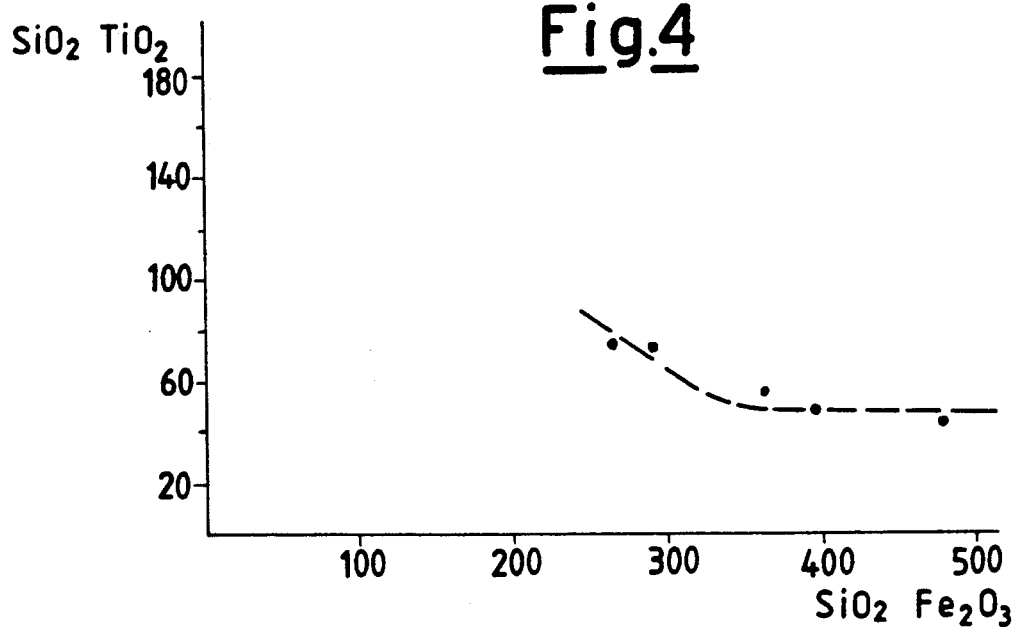

In FIG. 4, a chart is depicted, which sets forth the dependence of the maximum amounts of titanium (shown as $SiO_2/TiO_2$ molar ratio) and of iron (shown as $SiO_2/Fe_2O_3$ molar ratio) which can be obtained in the end product.

The I.R. spectrum of FIG. 1 is essentially similar to that of the zeolite as disclosed in BE-886,812 patent, whilst it is considerably different from that of ZSM-5 (or from similar structures) and from that of the ferrosilicate as disclosed in FR-2,403,975 patent application, which have the I.R. spectrum as shown in FIG. 2. It can be observed that in the spectrum of FIG. 2, the band at 965-975 cm$^{-1}$, which is characteristic of titanium silicalite of BE-886,812, and of titanium-iron-silicalite, does not appear.

Summarizing, the material as disclosed by ourselves is different from ZSM-5 of U.S. Pat. No. 3,702,886 and from the ferrosilicate as of FR-2,403,975 patent application, as to both its empirical formula and its I.R. spectrum; and relatively to the zeolite of BE-886,812 patent as to its empirical formula.

Furthermore, the use of the subject material of the present invention as a catalyst in the above listed reactions is a further confirmation of the difference of our product relatively to those of the prior art.

In fact, both ZSM-5 of U.S. Pat. No. 3,702,886, and the ferrosilicate of FR-2,403,975 patent application can be used as catalysts in such reactions as dehydrations of oxygenated organic compounds, cracking, selectoforming, hydrogenations and dehydrogenations, oligomerizations, alkylations, isomerizations, but they result inactive in the reactions between organic substrates and $H_2O_2$ (hydroxylation of phenol to diphenols, oxidation of olefins), whilst the zeolite of BE-886,812 results inactive for the first reactions and active for the last ones; to the contrary, our zeolite is active for all of the above mentioned reactions.

A second object of the present invention is the preparation process for the obtainment of the synthetic, crystalline, porous material as defined above.

Said process is characterized in that under hydrothermal conditions a derivative of silicon, a derivative of titanium, a derivative of iron and a nitrogenous organic base are reacted, with an $SiO_2/Fe_2O_3$ molar ratio of the reactants greater than 50, preferably comprised within the range of from 150 to 600, an $SiO_2/TiO_2$ molar ratio of the reactants greater than 5, preferably comprised within the range of from 15 to 25, an $H_2O/SiO_2$ molar ratio of the reactants preferably comprised within the range of from 10 to 100, more preferably of from 30 to 50, possibly in the presence of one or more salts and/or hydroxides of alkali or alkali-earth metals, with an $M/SiO_2$ molar ratio (wherein M is the alkali and/or alkali-earth cation) of the reactants lower than 0.1, preferably lower than 0.08, or equal to zero.

In the empirical formula of the material, the iron has been indicated in the $HFeO_2$ form, to underline that the material is in the $H^+$ form. When speaking of the ratios between the various reactants, we use, for iron, the $Fe_2O_3$ form, which is the most usual.

The silicon derivative is selected from silica gel, silica sol and alkyl silicates, among which, preferably, tetraethyl silicate; the titanium derivative is selected from titanium salts, such as, e.g., its halides, and organic titanium derivatives, such as, e.g., alkyltitanates, preferably tetraethyl titanate; the iron derivative is selected from iron salts, such as, e.g., its halides or the nitrates, the hydroxides, and the organic derivatives, such as, e.g., the alkoxides.

The nitrogenous organic base can be an alkylammonium hydroxide, preferably tetrapropyl-ammonium hydroxide.

In case tetrapropylammonium hydroxide is used, the $TPA^+/SiO_2$ ratio (wherein TPA=tetrapropylammonium) of the reactants is comprised within the range of from 0.1 to 1, preferably from 0.2 to 0.4.

The reactants are reacted with each other by operating at a temperature of from 100° to 200° C., preferably of from 160° to 180° C., at a pH comprised within the range of from 9 to 14, preferably of from 10 to 12, and for a time period ranging from 1 hour to 5 days, preferably from 3 hours to 10 hours.

To the purpose of better illustrating the meaning of the present invention, some preparation and use examples are given, which in no way are to be considered as being limitative of the same invention.

EXAMPLE 1

This example shows the preparation of titanium-iron-silicalite.

0.65 g of $Fe(NO_3)_3.9H_2O$ is dissolved in water and from the solution the hydroxide is precipitated by means of the addition on ammonium hydroxide. The precipitate is filtered and washed by being redispersed in cold water, and filtered until the filtrate turns to neutral. The damp hydroxide is then dissolved in 54 g of solution at 18.7% by weight of tetrapropyl-ammonium hydroxide.

In a separate vessel, 2.28 g of tetraethyl-orthotitanate is dissolved in 41.6 g of tetraethyl-silicate and this solution is added to the previously prepared one, with stirring.

The whole mass is heated at 50°-60° C., always with stirring, until a single-phase solution is obtained, then 100 cc of water is added.

The obtained solution is charged to an autoclave and is heated, under its autogenous pressure, at 170° C. over 4 hours.

The discharged product is centrifuged and washed twice by re-dispersion and centrifuging; it is then dried 1 hour at 120° C., and is then calcined 4 hours at 550° C. in the air.

The obtained product has an $SiO_2/Fe_2O_3$ molar ratio of 394, and an $SiO_2/TiO_2$ molar ratio of 48.

EXAMPLES 2-6

In Table 1 other titanium-iron-silicalites are shown, which have been prepared by the same modalities as disclosed in Example 1, but with the composition of the reactants being varied.

From the above-reported preparation examples, one can observe that the maximum amounts of titanium and iron which can be obtained in the end product are not independent from each other.

The minimum $SiO_2/TiO_2$ ratio which can be obtained is of about 44, and it can be only obtained if $SiO_2/Fe_2O_3$ ratio in the reactant mixture is higher than about 250 (Examples 1, 2, 3).

By increasing $SiO_2/Fe_2O_3$ ratio in the reactant mixture, a decrease of $SiO_2/TiO_2$ ratio and an increase of $SiO_2/Fe_2O_3$ occurs in the obtained product (Examples 5, 4, 1, 2, 3).

$SiO_2/TiO_2$ ratio in the obtained product continues to decrease until it reaches its minimum value around 44, which is reached when $SiO_2/Fe_2O_3$ in the reaction mixture is of from 250 to 600; further increases of $SiO_2/Fe_2O_3$ ratio in the reactant mixture cause only $SiO_2/Fe_2O_3$ to increase in the obtained product, whilst $SiO_2/TiO_2$ remains nearly constant (Example 3).

The addition of alkali metals to the reaction mixture favours the decrease of $SiO_2/Fe_2O_3$ ratio in the obtained product (Example 6) ratio in the obtained product.

EXAMPLE 7

Always in Table 1, a product is shown, which does not have the same characteristics as of the preceding products.

It can be observed from said Example that, when the $SiO_2/Fe_2O_3$ ratio in the reactant mixture is 30, in the absence of alkali metals no crystallization of the mixture occurs.

EXAMPLE 8

Always in Table 1, a product is shown, which has the I.R. spectrum of FIG. 3, from which it can be observed that the band at 965-975 cm$^{-1}$ is only sparingly shown, with a much lower intensity than that in the spectrum of FIG. 1, although the product of Example 8 has a higher titanium content than of Examples 1-3.

The addition of large amounts of alkali metals (M+/SiO$_2$_0.08) in the reaction mixture can cause an increase in titanium amount, which can be detected from the chemical analysis of the obtained product, an SiO$_2$/TiO$_2$ ratio lower than 40 being obtained, but is such case TiO$_2$ is at least partly in a form different from the form it has in the titanium-iron-silicalite, and such as not to yield the spectrum of FIG. 1, but that of FIG. 3.

In FIG. 4, a chart is shown, which sets forth the dependence of the maximum amounts of titanium (shown in the ordinates as SiO$_2$/TiO$_2$ molar ratio) and of iron (shown in the abscissae as SiO$_2$/Fe$_2$O$_3$ molar ratio) which can be obtained in the end product.

TABLE 1

| Example | Reaction Mixture Composition | | | | | Crystallization time, hours | Crystallization Temperature, °C. | Product Composition | |
|---|---|---|---|---|---|---|---|---|---|
| | SiO$_2$/Fe$_2$O$_3$ | SiO$_2$/TiO$_2$ | Na+/SiO$_2$ | TPA+/SiO$_2$ | H$_2$O/SiO$_2$ | | | SiO$_2$/Fe$_2$O$_3$ | SiO$_2$/TiO$_2$ |
| 1 | 250 | 20 | — | 0.25 | 40 | 4 | 170 | 394 | 48 |
| 2 | 600 | 20 | — | 0.25 | 40 | 4 | 170 | 474 | 43 |
| 3 | 1000 | 20 | — | 0.25 | 40 | 4 | 170 | 837 | 44 |
| 4 | 200 | 20 | — | 0.25 | 40 | 4 | 170 | 363 | 55 |
| 5 | 70 | 20 | — | 0.25 | 40 | 4 | 170 | 287 | 72 |
| 6 | 200 | 20 | 0.01 | 0.25 | 40 | 4 | 170 | 262 | 73 |
| 7 | 30 | 20 | — | 0.25 | 40 | 4 | 170 | no crystallization | |
| 8 | 70 | 20 | 0.08 | 0.25 | 40 | 15 | 170 | 54 | 23 |

EXAMPLE 9

To a 1-l steel autoclave equipped with mechanical stirrer, temperature control system, pressure control system to operate under constant pressure, 70 g of water, 250 g of methanol, 4 g of catalyst prepared according to Example 2 are charged.

To a drum connected with the autoclave, 54 g of 34% (weight/weight) H$_2$O$_2$ is charged. After that the temperature of the system has been set at the controlled value of 40° C., and being pressurized with propylene at the pressure of 6 abs. atm. (constant throughout the test duration), the hydrogen peroxide is added, with strong stirring, to the suspension inside the autoclave.

The reaction is monitored by samples being drawn, at time intervals, and analysed. Hydrogen peroxide is determined by iodometric titration, and the reaction products are analysed by gas-chromatography.

After 1 hour the following situation has occurred:

| H$_2$O$_2$ conversion | 95% |
|---|---|
| Selectivity (relatively to H$_2$O$_2$), | |
| propylene oxide | 80% |
| 1-methoxy-2-hydroxypropane | 11% |
| 2-methoxy-1-hydroxypropane | 5.5% |
| propylene glycol | 3.0% |

EXAMPLE 10

The process is carried out by means of the equipment and the modalities of Example 9. The reactants used are 420 g of CH$_3$OH, 4 g of catalyst (prepared according to Example 2) and 41 g of 34% (weight/weight) H$_2$O$_2$. The operating temperature is of 40° C. and the propylene pressure is of 4 abs. atm. After 45 minutes of reaction, the situation of the system is as follows:

| H$_2$O$_2$ conversion | 93% |
|---|---|
| Selectivity (relatively to H$_2$O$_2$), | |
| propylene oxide | 83% |
| 1-methoxy-2-hydroxypropane | 10% |
| 2-methoxy-1-hydroxypropane | 5.5% |
| propylene glycol | 1% |

EXAMPLE 11

To a 1-l steel autoclave, equipped with mechanical stirrer and reaction temperature control system, 450 g of methanol 90 g of 1-octene, 4.5 g of catalyst (prepared according to Example 2) are charged.

To a drum connected with the autoclave, 45 g of 34% (weight/weight) H$_2$O$_2$ is charged. After that the temperature of the system has been set at the controlled value of 45° C., and with stirring, hydrogen peroxide is added to the other reactants. The reaction course is monitored by samples being drawn at regular time intervals. Hydrogen peroxide is determined by iodometric titration, and the reaction products are analysed by gas-chromatography.

After 1 hour, the situation is:

| H$_2$O$_2$ conversion | 90% |
|---|---|
| Octene conversion | 50.3% |
| Selectivity to 1,2-epoxyoctane | 78% |
| Ethers + glycols | 21.5% |

EXAMPLE 12

The process is carried out by means of the same modalities and equipment as of Example 11.

To the autoclave, charged are 400 g of methanol, 90 g of allyl chloride, and 9 g of catalyst prepared according to Example 2; to the drum, 61 g of 34% (weight/weight) H$_2$O$_2$ is added. The reaction is carried out at the temperature of 60° C. Thirty minutes later, the situation is:

| H$_2$O$_2$ conversion | 95% |
|---|---|
| Allyl chloride conversion | 49% |
| Epichlorohydrin selectivity (relatively to H$_2$O$_2$) | 80% |

EXAMPLE 13

To a tubular steel reactor, 1.04 g is charged of catalyst of 18-40 mesh of granulometry, prepared according to Example 2. The reactor is placed inside and electrical oven and is gradually heated up to the reaction temperature, with a stream of dimethyl ether being flown through it. The gaseous reaction products are analyzed by in-line chromatography after the liquid products being condensed in a bath kept at 0°-5° C. These latter are separately weighed and analyzed, always by chromatographic way. The conversion and selectivity are computed according to the hereunder shown equations:

$$\text{Conversion} = \frac{(DME_{in} - DME_{out})}{(DME_{in})}$$

$$\text{Selectivity} = \frac{(\text{mol of } i \text{ product})}{(DME_{in} - DME_{out})}$$

($DME$ = dimethyl ether; in = incoming; out = outgoing).

The reaction conditions and the results obtained are gathered in Table 2.

TABLE 2

| T | (°C.) | 360 | 380 |
|---|---|---|---|
| p | (atm) | 1 | 1 |
| GHSV | (h$^{-1}$) | 440 | 800 |
| Run hours | | 3 | 3 |
| DME Conversion | (%) | 86 | 84 |
| Product Composition (% by weight - H$_2$O, DME excluded) | | | |
| CH$_3$OH | | 11.0 | 67.2 |
| CH$_4$ | | 0.4 | 0.5 |
| C$_2$H$_4$ | | 0.7 | 0.7 |
| C$_2$H$_6$ | | 0.01 | 0.01 |
| C$_3$H$_6$ | | 8.6 | 18.6 |
| C$_3$H$_8$ | | 0.1 | 0.3 |
| ΣC$_4$ | | 2.7 | 9.6 |
| ΣC$_5$ | | 0.3 | 1.9 |
| ΣC$_6$+ | | 76.1 | 1.1 |

We claim:

1. Process for preparing a synthetic crystalline and porous material having a zeolite nature, containing oxides of silicon, titanium and iron, having, in its calcined and anhydrous state the empirical formula:

pHFeO$_2$.qTiO$_2$.SiO$_2$ wherein p has a value greater than zero and smaller than or equal to 0.050, and q has a value greater than zero and smaller than or equal to 0.025, the hydrogen of HFeO$_2$ being at least partially substitutable by cations, said process comprising: reacting under hydrothermal conditions a source of silicon, a source of titanium, a source of iron and a nitrogenous organic base, with a SiO$_2$/Fe$_2$O$_3$ molar ratio in the reaction mixture greater than 50, with a SiO$_2$/TiO$_2$ molar ratio in the reaction mixture greater than 5, and with a H$_2$O/SiO$_2$ molar ratio from 10 to 100, at a temperature from 120° C. to 200° C., at a pH from 9 to 14 and for a time from 1 hour to 5 days.

2. The process according to claim 1, wherein in the reaction mixture the SiO$_2$/Fe$_2$O$_3$ molar ratio is between 150 and 600, the SiO$_2$/TiO$_2$ molar ratio is between 15 and 25, and the H$_2$O/SiO$_2$ molar ratio is between 30 and 50.

3. The process according to claim 1, wherein said silicon source is selected from the group consisting of silica gel, silica sol and alkyl silicates, said titanium source is selected from salts and organic sources of titanium, said iron source is selected from the group consisting of salts, hydroxides and organic sources of iron.

4. The process according to claim 3, wherein said alkyl silicates are tetraethyl silicate.

5. The process according to claim 3, wherein said titanium salts are halides.

6. The process according to claim 3, wherein said organic sources of titanium are alkyl titanates.

7. The process according to claim 6, wherein said alkyl titanates are tetraethyltitanate.

8. The process according to claim 3, wherein said iron salts are selected from the group consisting of halides and nitrates.

9. The process according to claim 3, wherein said organic sources of iron are alkoxides.

10. The process according to claim 1, wherein said organic base is alkylammonium hydroxide.

11. The process according to claim 10, wherein said alkylammonium hydroxide is tetrapropylammonium hydroxide.

12. The process according to claim 1, wherein said process occurs at a temperature from 160° C. to 180° C., at a pH from 10 to 12 and for a time ranging from 3 hours to 10 hours.

13. The process according to claim 11, wherein in the reaction mixture a TPA+/SiO$_2$ molar ratio is from 0.1 to 1.

14. The process according to claim 13, wherein in the reaction mixture said TPA+/SiO$_2$ molar ratio is from 0.2 to 0.4.

15. The process according to claim 1 wherein the reaction is conducted in the presence of one or more salts and/or hydroxides of alkali metals or alkaline earth metals, with a M+/SiO$_2$ molar ratio in the reaction mixture, wherein M+ is an alkali-metal or an alkaline earth metal cation, smaller than 0.10.

16. The process according to claim 1 wherein in the reaction there is a SiO$_2$/Fe$_2$O$_3$ molar ratio in the crystalline material higher than about 250 and a SiO$_2$/TiO$_2$ molar ratio in the crystalline material of about 44 is produced.

17. The process according to claim 16 wherein in the reaction mixture there is a SiO$_2$/Fe$_2$O$_3$ molar ratio in the crystalline material higher than about 250 and a SiO$_2$/TiO$_2$ molar ratio in the crystalline material of about 44 is produced.

* * * * *